(12) United States Patent
Mezzoli et al.

(10) Patent No.: US 12,220,548 B2
(45) Date of Patent: Feb. 11, 2025

(54) DISPENSER

(71) Applicants: Giorgio Mezzoli, Lugo (IT); Maria Rani, Lugo (IT)

(72) Inventors: Giorgio Mezzoli, Lugo (IT); Maria Rani, Lugo (IT)

( * ) Notice: Subject to any disclaimer, the term of this patent is extended or adjusted under 35 U.S.C. 154(b) by 946 days.

(21) Appl. No.: 16/321,488

(22) PCT Filed: Jul. 28, 2017

(86) PCT No.: PCT/IB2017/054617
§ 371 (c)(1),
(2) Date: Jan. 29, 2019

(87) PCT Pub. No.: WO2018/025139
PCT Pub. Date: Feb. 8, 2018

(65) Prior Publication Data
US 2021/0283384 A1    Sep. 16, 2021

(30) Foreign Application Priority Data
Aug. 1, 2016  (IT) .......................... 102016000080879

(51) Int. Cl.
*A61M 11/00* (2006.01)
*A61M 31/00* (2006.01)
(Continued)

(52) U.S. Cl.
CPC ............ *A61M 31/00* (2013.01); *A61M 11/00* (2013.01); *A61M 11/001* (2014.02); *B05B 1/10* (2013.01);
(Continued)

(58) Field of Classification Search
CPC .... A61M 31/00; A61M 11/00; A61M 11/001; B05B 1/10; B05B 1/34
See application file for complete search history.

(56) References Cited

U.S. PATENT DOCUMENTS 3,176,883 A * 4/1965 Davis, Jr. ............... A61M 11/00
239/327
4,961,727 A * 10/1990 Beard .................... A61M 11/00
128/200.22
(Continued)

FOREIGN PATENT DOCUMENTS

CN    102665642 A    9/2012
EP    0534088 A1    3/1993
(Continued)

OTHER PUBLICATIONS

International Search Report and Written Opinion Received for the PCT Application No. PCT/IB2017/054617 mailed on Nov. 3, 2017, 8 pages.

*Primary Examiner* — Timothy A Stanis
(74) *Attorney, Agent, or Firm* — Leason Ellis LLP

(57) ABSTRACT

Dispenser (1) for liquids comprising an applying nozzle constituted by a bell-shaped body (2) extending along a central axis (A) and provided, at the bottom, with an annular collar (3) and, at the top, with a convex cap (4); the bell-shaped body (2) having a first axial hole (5) whose cross-section decreases from the collar (3) towards said cap (4); a valve (7) for nebulizing the solution being housed inside the first hole (5) in a matching manner; an expansion device (9) being provided at the exit of said first hole (5).

17 Claims, 2 Drawing Sheets

(51) Int. Cl.
*B05B 1/10* (2006.01)
*B05B 1/34* (2006.01)
*B65D 83/28* (2006.01)
*B65D 83/48* (2006.01)

(52) U.S. Cl.
CPC ................ *B05B 1/34* (2013.01); *B65D 83/28* (2013.01); *B65D 83/48* (2013.01)

(56) References Cited

U.S. PATENT DOCUMENTS

| | | | | | |
|---|---|---|---|---|---|
| 5,031,800 | A * | 7/1991 | Brunet | ................ | B65D 83/224 128/200.23 |
| 6,228,070 | B1 | 5/2001 | Mezzoli | | |
| 8,486,029 | B2 * | 7/2013 | Cacka | ................ | A61M 3/022 604/73 |
| 8,801,667 | B2 * | 8/2014 | Taylor | ................ | A61M 3/0279 604/118 |
| 8,991,660 | B2 * | 3/2015 | Hair | ................ | B65D 1/32 222/211 |
| 2002/0170928 | A1 * | 11/2002 | Grychowski | ........ | B65D 83/386 222/251 |
| 2003/0226907 | A1 * | 12/2003 | Geser | ................ | B05B 1/26 239/398 |
| 2006/0138254 | A1 | 6/2006 | Bougamont et al. | | |
| 2008/0272144 | A1 * | 11/2008 | Bonney | ................ | A61M 15/009 222/71 |
| 2010/0163582 | A1 * | 7/2010 | Collins | ................ | B05B 11/007 222/321.6 |
| 2012/0199119 | A1 | 8/2012 | Pardonge | | |
| 2012/0277678 | A1 * | 11/2012 | Taylor | ................ | A61M 3/0258 604/153 |
| 2013/0068797 | A1 * | 3/2013 | Laidler | ................ | B05B 11/3095 222/321.6 |
| 2014/0170081 | A1 * | 6/2014 | Muller | ................ | A61K 31/58 128/200.23 |

FOREIGN PATENT DOCUMENTS

| | | |
|---|---|---|
| EP | 1092447 A2 | 4/2001 |
| FR | 2812826 A1 | 2/2002 |

\* cited by examiner

DISPENSER

RELATED APPLICATIONS

This application is a National Stage application of International application PCT/IB2017/054617, filed Jul. 28, 2017 and which claims priority of Italian application 10 2016 0000 808 filed Jul. 28, 2017 both applications are incorporated herein by reference thereto.

The present invention relates to a dispenser for dispensing nebulized liquid solutions. In particular, the present invention relates to a dispenser for dispensing nebulized liquid solutions, which is provided with a spray valve. In more detail, the present invention relates to a dispenser for dispensing nebulized liquid solutions through a dispensing body containing a nebulizing valve.

BACKGROUND TO THE INVENTION

As used herein, the term "solution(s)" means any type of solution, including a drug solution or a pharmacologically active solution applied in the form of spray, aerosol, micronized shower, nebulization, as well as a solution for washing the nasal passages, the mouth cavity, the vaginal cavity, the outer ear canal, or applied on healthy and/or damaged skin, in order to treat or to prevent local inflammatory diseases or diseases communicable through the above mentioned body areas. It should also be specified that, as used herein, the term "nebulized" refers to a liquid solution and indicates that this solution has been broken up into particles, without specifying the dimensions thereof.

A particular problem is represented by washing the nasal passages. Usually, in order to wash the nasal cavities, the washing solution is made flow inside a cavity and exit outside from the other cavity through the nasopharynx, thus mechanically removing any pathological secretion; during the wash, the head shall be inclined forwards, and it is necessary to breathe through the mouth, that shall be open during the whole operation in order to prevent the solution from flowing into the low respiratory tracts and causing difficulties in nose breathing or, in most severe cases, bronchial spasm. It shall be also specified that nose wash is not suitable for patients of any age. For example, it is not suitable for infants.

With these patients, the problem is solved by nebulizing the solution in particles of given diameter based on the patient's age and the therapy/treatment to be performed, using nebulizing valves of different conformation so that the nebulized solution propagates inside the nose cavities in a specific way. For this reason, the administration of a solution in the form of spray, aerosol, micronized shower, nebulizing inside the nose cavities is used instead of nose washes for infants, children or in general for low collaborative or bedridden patients.

In particular, inside the nose cavities, that are particularly complex anatomical structures, the solution shall be distributed in a diffused and homogeneous manner; this is possible only if the turbulence degree is so high as to be similar to the natural turbulence degree of the air passing through the nose passages while breathing before achieving the low respiratory tracts. Moreover, in certain cases, when the nebulized solution has to be directed uniformly in the whole nose cavity to be treated, it is necessary that the turbulence degree of the nebulized solution is maximum so as to touch the nose mucosa in a diffused and homogeneous manner.

In the known devices, the liquid nebulization degree only depends on the type of nebulizing valve arranged inside and at the top of the dispensing nozzle. Two examples of known dispensers are illustrated in FIG. 1A (bottle) and FIG. 1B (syringe), where a bottle 29 is shown, containing the solution to be administered. The bottle 29 comprises a dispensing valve inserted inside and at the top of an applying nozzle. Through a hole of reduced diameter provided in top position, the solution contained in the bottle 29 exits, in the form of nebulized jet G (schematically shown in figures 1A and 1B), from the valve 29b. The same applies for the syringe of figure 1B. It is therefore easily understood that it would be desirable to have available a dispenser suitable to nebulize a solution increasing the turbulence degree thereof, and therefore the propagation degree, so that the solution is better diffused inside the anatomical cavity to be treated, for example, although without limitation, the nose cavities, the mouth, the outer ear canal, the vaginal cavity, or on the healthy or damaged skin. In addition, such a product could define a new standard for the dispensers of solutions and inhalants, in order to limit and, possibly, to overcome the prior art drawbacks mentioned above.

SUMMARY OF THE PRESENT INVENTION

The present invention relates to a dispenser for dispensing nebulized liquid solutions. In particular, the present invention relates to a dispenser for dispensing nebulized liquid solutions, which is provided with a spray valve. In more detail, the present invention relates to a dispenser for dispensing nebulized liquid solutions through a dispensing body containing a nebulizing valve.

An object of the present invention is to provide a dispenser that is devoid of the drawbacks described above and that allows to dispense liquid solutions in the form of particles organized in jet, spray, aerosol, micronized shower, the particles being diffused with a high turbulence degree.

According to the present invention a simple and economical dispenser is provided, allowing to dispense liquid solutions in nebulized form according to the user's specific needs as described in at least one of the appended claims.

A further object of the present invention is to provide a dispensing device for dispensing a liquid solution that is simple and economical and incorporates at least one dispenser devoid of the drawbacks described above and that therefore allows to dispense liquid solutions in the form of particles organized in jet, spray, aerosol, micronized shower, the particles being diffused with a high turbulence degree.

According to the present invention a simple and economical dispensing device for liquid solutions is provided, incorporating at least a dispenser suitable to break up the solutions into particles organized in the form of jet, spray, aerosol, micronized shower, according to the user's specific needs as described in at least one of the appended claims.

BRIEF DESCRIPTION OF DRAWINGS

The invention will be better described with reference to non-limiting embodiments illustrated in the attached figures, where.

DETAILED DESCRIPTION OF THE PRESENT INVENTION

Figure 1A:
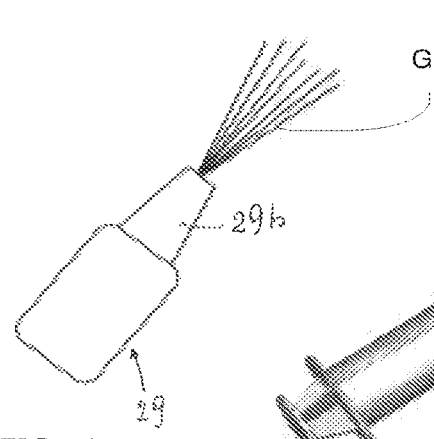
FIGS. 1A and 1B schematically illustrate two embodiments of two dispensers according to the prior art.
Figure 1B:
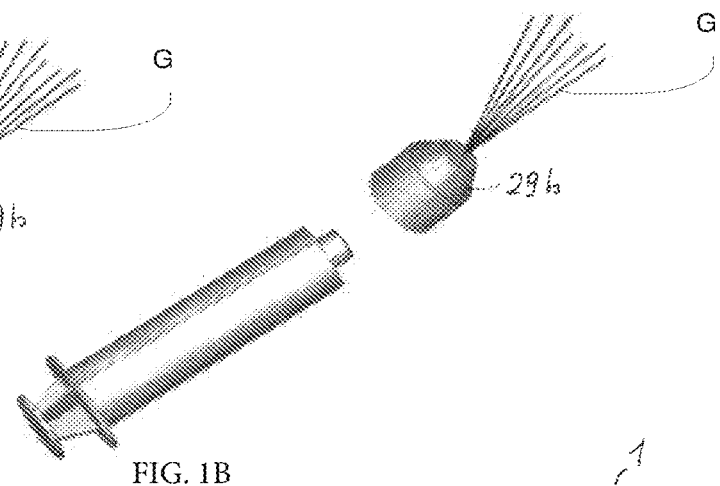
Figure 2:
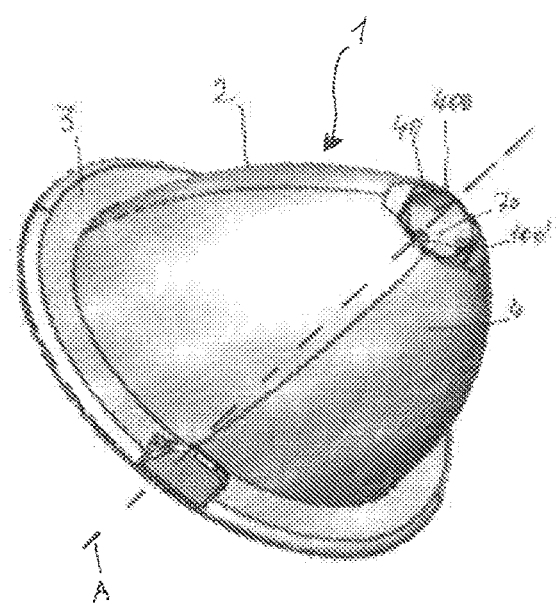
FIG. 2 is a schematic perspective view from the top of a dispenser according to the present invention.
Figure 3:
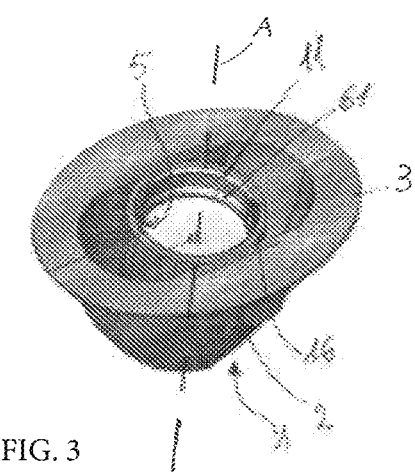
FIG. 3 is a schematic perspective view from the bottom of FIG. 2.
Figure 8:
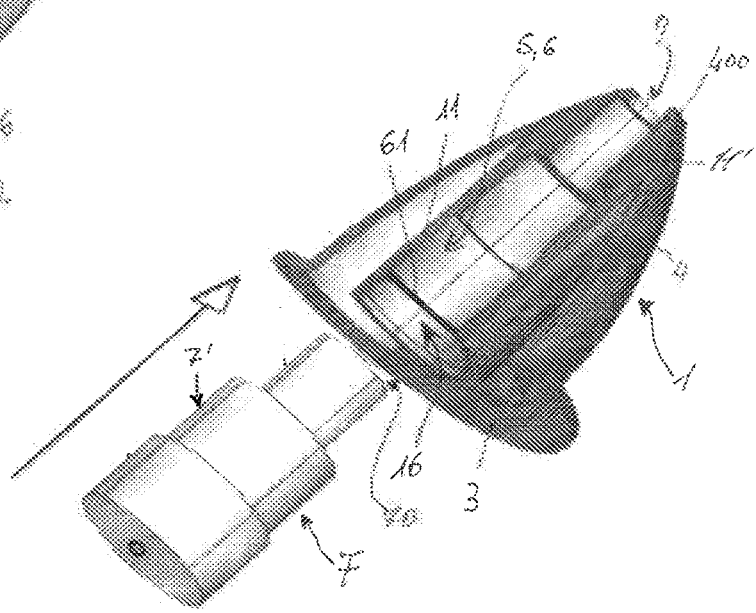
FIG. 8 is an exploded view of FIG. 4.

In FIG. 2, number 1 indicates a dispenser 1 for liquid solutions; the dispenser 1 comprises an applying nozzle constituted by a bell-shaped body 2 extending along a central axis A starting from an annular collar 3 with a convex cap-shaped portion 4. The bell-shaped portion 2 stably carries an elongated rigid body 11, substantially concentric with the axis A and provided with a first through hole 5 (FIG. 3). The first hole 5 is peripherally delimited by a surface, whose cross-section decreases starting from the collar 3 towards the cap 4 (better shown in FIG. 8), and has an end portion 40 delimited at the top by an axial opening 400. In particular, the cap 4 carries the cylindrical body 11 through an end portion 11' thereof. Without limiting the scope of the present invention, the first hole 5 has a plurality of cylindrical segments 60 which are concentric with the axis A and whose diameter decreases starting from the collar 3, as shown in any one of FIGS. 4-7. The bell-shaped body 2 (the applying nozzle) is usually made of flexible plastic, for example PVC, without however limiting the scope of the present invention. In fact, in some cases the bell-shaped body 2 shall be partially deformable so as better to adapt to the shape of the nasal cavity or other anatomical cavity where the nebulized liquid solution shall be applied. The bell-shaped body 2 (the applying nozzle) may be made of ABS or other plastic having mechanical features similar to those of ABS, without however limiting the scope of the present invention.

The dispenser 1 also comprises a valve 7, better shown in FIG. 3, for breaking up liquid solutions into particles of given dimension and to organize them in a jet G inside the end portion 40. The valve 7 has a longitudinal (axial) channel 100 and is housed in the first hole 5 in a removable manner so as to be interchangeable with an outer surface 7' (better shown in FIG. 8) coupled to a longitudinal portion of the first hole 5 in a matching manner. Even if in the attached figures the valve 7 is always illustrated with only one central channel 100, this does not limit the scope of the present invention; in fact, depending on the treatment to be performed, the valve 7 may have only one central hole constituted by the channel 100, or a plurality of longitudinal holes arranged in a given manner with respect to the axis A. Obviously, in case the valve has more holes, having reduced cross-section with respect to the illustrated case, it is possible to have a thinner nebulization of the liquid solution given the same feed pressure.

The jet shape inside the end portion 40 and outside the bell-shaped body obviously depends on the geometrical characteristics of the valve 7, i.e. on the conformation of the channel 100 or on the presence of a plurality of longitudinal holes, and on the pressure at which the liquid solution is supplied to the valve 7.

As shown in FIGS. 4-7, the opening 400 is spaced from an upper face 70 (shown only in FIG. 2) of the valve 7 by a length L. In particular, the channel 100 is substantially cylindrical and the end portion of the first hole 5 has a discharge chamber 10 delimited peripherally by the end portion 40 of the first hole 5, at the top by the opening 400 and at the bottom by the upper face 70. The chamber 10, as well as the end portion 40, has longitudinal cross section of given shape, as it will be better described below, so as to give the jet G a given shape. This particular arrangement of the chamber 10 allows the corresponding portion 40 to deviate, in use, the propagation direction of the particles into which the liquid solution has been broken up by the valve 7, as better described below.

Figure 4:
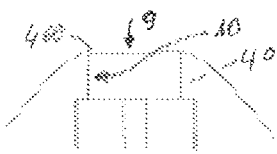
FIGS. 4-7 are longitudinal cross-sectional views of FIG. 2.
Figure 5:
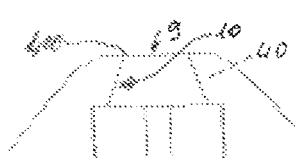
Figure 6:
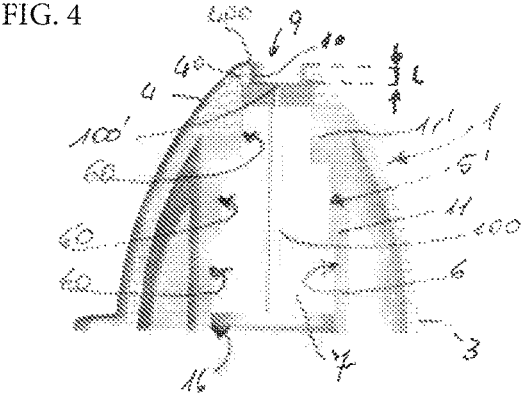
Figure 6:
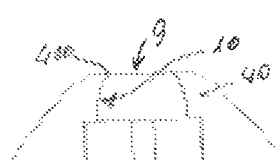
Figure 7:
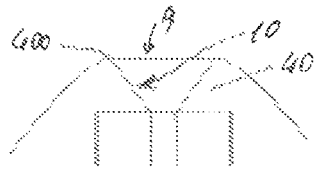

Without departing from the protective scope of the present invention, the longitudinal cross section of the chamber 10 may selectively be cylindrical, as in FIG. 4, conical decreasing towards the top, like an overturned funnel as in FIG. 5, or shaped as shown in FIG. 7, where the longitudinal conical cross section of the corresponding end portion 40 is flared, or increases towards the top, like a funnel. FIG. 6 shows a chamber 10 shaped like an overturned funnel wherein the walls of the funnel are substantially hemispherical, like a dome, whose cross section decreases towards the outside. Moreover, the chamber 10 and/or the opening 400 delimiting the chamber 10 at the top, and therefore also the end portion 40 delimiting the chamber 10 peripherally, may be indifferently shaped like a circle, an oval or an ellipse, and therefore the longitudinal cross-section of the corresponding chamber 10 may be conical or cylindrical.

Figure 9:
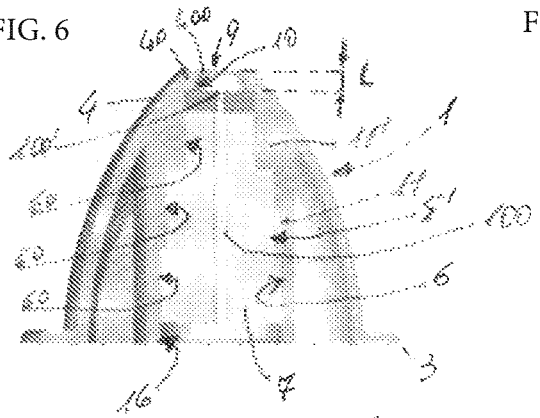
FIG. 9 is a schematic perspective view in reduced scale of FIG. 3 in an operative configuration.
Figure 9:
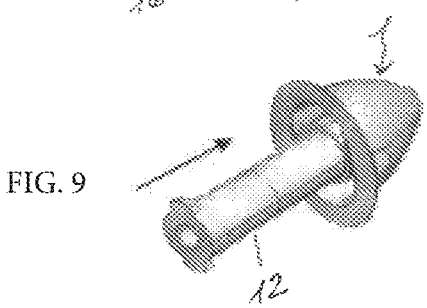

In order to achieve a high turbulence degree of the nebulized liquid, the axial length L of the chamber 10 shall preferably be comprised between 2 and 5 mm, without however limiting the scope of the present invention, as the actual height of the chamber may be defined according to the specific needs. It should be useful to specify that, for the same reason again, the maximal cross section of the end portion 40 of the chamber 10 is comprised between 2 and 5 mm and the minimal cross section is comprised between 1 and 5 mm.

The different conformation of the chamber 10 results in a change of the propagation direction of the particles exiting from the channel 100 and the change of the dimension of the particles forming the jet G; these changes cause a different conformation of the jet G and a different ability in penetrating the cavities to be treated. In other words, what gives a given shape and propagation direction to the particles forming the jet G into which the liquid solution fed to the valve 7 has been broken up is the particular conformation of the valve 7 and of the surface delimiting the end portion 40 inside the chamber 10. Therefore, herein the chamber 10 will be considered the essential part of a deviation device 9 with which the dispenser 1 is provided, the device, and therefore the chamber, having the function of interacting with the particles into which, in use, the liquid solution exiting from the channel 100 (of the valve 7) has been broken up, in order to modify the dimension and propagation direction of the particles, and therefore in order to modify the shape and propagation direction of the jet G in which the particles are organized. It is easily understood that the change of these parameters of the jet G can be visually seen outside the dispenser 1, but they are a consequence of how the particles of the liquid solution are treated inside the chamber 10.

With particular reference to FIG. 3, a ring 61 is illustrated, which is made in a single piece with the cylindrical body 11; the ring acts as lower abutment for the valve 7, so as to keep it in place inside the cylindrical body 11. Obviously, the ring 61 is flexible and thus allows easily to insert the valve 7 in, and to remove the valve from, the cylindrical body 11, according to the needs of dispensing the liquid solution broken up into particles of given dimension and with a given propagation direction according to the user's needs.

With reference to FIGS. 4-7 it should be specified that the first hole 5 is longitudinally engaged by the valve 7 partially, so as to leave a portion thereof free, the portion defining a housing 16 delimited at the top by the ring 61, not shown in the figures for the sake of drawing economy. The housing 16 can be freely engaged by a connector 12 at approximately the height of the collar 3, shown in FIG. 9. The connector 12 may usefully have an end shaped like a female connection of a Luer lock, a known fluid-tight threaded coupling, without however limiting the scope of the invention. In this case, thanks to the use of the connector 12, the dispenser 1 can indifferently interface syringes and rigid or flexible tubes provided with male connection for Luer locks.

The use of the dispenser 1 is easily understood from the description above and does not require further explanations. However, it should be useful to specify that, as regards the nose cavities treatment, the dispenser 1 can be usefully used by bringing the cap 4 into contact with the nostril so that the chamber 10, and therefore the opening 400, is completely contained inside the nostril. At this point, the dispenser 1 can be supplied with the liquid solution through the valve 7. The solution is then nebulized in the passage inside the channel 100 and is deviated by the walls of the end portion 40 of the chamber 10, due to the particular combination of feeding pressure and conformation of the chamber 10. In this way, the jet G, into which the liquid solution has been nebulized, will be finely dispersed in a diffused and homogeneous manner inside the nose cavity (or other cavity) to be treated. The particular conformation of the bell-shaped body 2 allows to treat nose cavities, mouth cavity, vaginal cavity, outer ear canal as well as healthy and/or damaged skin.

The increase in the turbulence of the nebulized liquid solution, whose aim is to increase the dispersion of the solution in the cavity to be treated, and therefore the effectiveness thereof, is achieved by combining the valve 7 and the expansion chamber 10, arranged in series at the top of the dispenser 1. To the different conformation of the expansion chamber 10 a different turbulence degree is associated, and therefore a different mode of propagation of the nebulized solution in the cavity and on the skin to be treated, given the same pressure on the solution and with the same valve 7.

In particular, as the pressure on the liquid solution to be dispensed increases inside the container hydraulically arranged upstream of the valve 7, the speed at which the solution exits from the channel 100 of the valve 7 increases proportionally, and proportionally increases the width of the jet wetting the side walls, and deviated by them, of the chamber 10 up to the edge 400 due to the different dimension of the particles into which the liquid solution has been broken up at the exit from the dispenser 1. In particular, inside the first hole 5, valves 7 may be inserted provided with an exit hole 100' of given dimensions, different than the dimension of the channel 100. This allows to modify the breaking up of the liquid solution into particles, that will have different dimension and will be consequently organized in different manners. It is easily understood that the shorter the transverse dimension of the hole 100', the lower the dimension of the particles into which the solution has been broken up/nebulized and the greater the width of propagation volume of the jet G.

In conclusion, in use, the liquid solution exits the channel 100 in a jet G, whose particles move forwards with different dimensions and different propagation direction than the original one outside the bell-shaped body 2 after having touched the end portion 40 peripherally delimiting the chamber 10, giving the jet G a shape that can be defined at will, based on the conformation of the valve 7 and of the walls of the chamber 10.

Lastly, it is clearly apparent that modification and variants can be done to the dispenser 1 described above without however departing from the protective scope of the present invention. For example, the collar 3 may be indifferently shaped like a circle, an oval or an ellipse. Moreover, in some cases the bell-shaped body 2 may be so constructed as to have a rigid structure, so as rigidly to incorporate the elongated body 11 to the cap 4.

Figure 10:
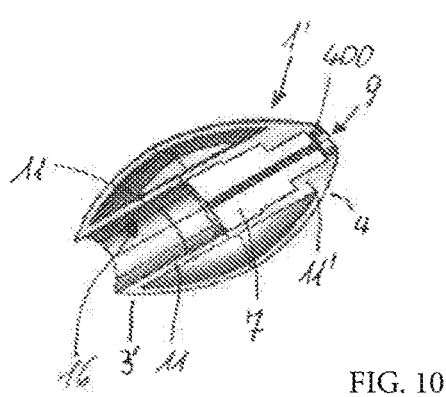
FIG. 10 is a variant of FIG. 2.

With particular reference to FIG. 10, a dispenser 1' is shown, whose bell-shaped body 2 is substantially shaped like an olive, so that the base portion 3' is rounded, replaces the collar 3 of FIGS. 2-9 and closes on the elongated body 11. For this reason, the dispenser 1' may be completely inserted in the cavity to be treated and may be easily removed therefrom without damaging the cavity. In view of the above description it is clearly apparent that the fact of maximizing the turbulence degree of a nebulized solution, simply by means of the particular conformation of the exit portion of the end portion 40 and of the valve 7 of the dispenser 1, makes the dispenser 1 customizable according to the needs and usable in different contexts, thus demonstrating great versatility of use at very low costs. Therefore, the dispenser 1 defines a new standard for the dispensers of solutions that can be inhaled or diffused inside body cavities, overcoming the drawbacks of the prior art in a simple and effective way.

The invention claimed is:

1. A dispenser for liquids comprising:
a valve provided with at least one longitudinal channel ending in at least one hole which is configured, in use, to break up liquid fed to said at least one longitudinal channel into small particles and form a jet stream having a predetermined shape;
a bell-shaped body having an outer surface with a rounded top and extending along a central axis and provided with an axial opening at the rounded top; said bell-shaped body comprising an inner surface from which an elongated member extends substantially concentric with said central axis, the elongated member defining an axial housing configured for receiving the valve; and
wherein said bell-shaped body comprises a deviation device with a discharge chamber of said jet stream arranged between an end face of said valve facing the axial opening and said axial opening and hydraulically connected with said at least one longitudinal channel in order to interact with said particles to modify a shape and direction of said jet stream;
wherein said axial opening defines a top end of the discharge chamber; wherein a width of the axial opening is greater than a width of the at least one hole that defines an exit of the valve;
wherein the valve has a stepped construction and the elongated member has a longitudinal hole that is peripherally delimited by the axial housing, the longitudinal hole defined by a plurality of cylindrical segments that are concentric with the central axis, wherein diameters of the plurality of cylindrical segments decrease in a direction toward the axial opening.

2. A dispenser for liquids comprising:
a valve provided with at least one longitudinal channel ending in at least one hole which is configured, in use, to break up liquid fed to said at least one longitudinal channel into small particles and form a jet stream having a predetermined shape;
a bell-shaped body having an outer surface with a rounded top and extending along a central axis and provided with an axial opening at the rounded top; said bell-shaped body comprising an inner surface from which an elongated member extends substantially concentric with said central axis, the elongated member defining an axial housing configured for receiving the valve; and wherein said bell-shaped body comprises a deviation device with a discharge chamber of said jet stream arranged between an end face of said valve facing the axial opening and said axial opening and hydraulically connected with said at least one longitudinal channel in order to interact with said particles to modify a shape and direction of said jet stream;

wherein said axial opening defines a top end of the discharge chamber; wherein a width of the axial opening is greater than a width of the at least one hole that defines an exit of the valve;

wherein the axial housing has a top shoulder against which a top end of the valve seats, the discharge chamber being located between the shoulder and the axial opening.

3. The dispenser according to claim 2, wherein said valve is shaped in order to be removable so as to be interchangeable; axial blocking means being provided for blocking said valve inside said housing.

4. The dispenser according to claim 3, wherein said axial blocking means comprises a ring coupled in a form-fitting manner to said housing at a base of said valve.

5. The dispenser according to claim 2, wherein said discharge chamber is peripherally delimited by an inner wall so configured as to deviate said jet stream.

6. The dispenser according to claim 5, wherein the height of said discharge chamber is comprised between 2 and 5 millimeters (mm).

7. The dispenser according to claim 5, wherein said inner wall has a maximum cross section comprised between 2 and 5 mm and a minimum cross section comprised between 1 and 5 mm.

8. The dispenser according to claim 2, wherein said discharge chamber has a longitudinal cross section of conical shape decreasing towards an exit in order to change the dimension and organization of said particles of said jet stream.

9. The dispenser according to claim 2, wherein said discharge chamber has a longitudinal cross section shaped like a dome of decreasing dimension towards an exit in order to change the dimension and organization of said particles of said jet stream.

10. The dispenser according to claim 2, wherein the rounded top of said bell-shaped body has an oval shape.

11. The dispenser according to claim 2, wherein said discharge chamber is cylindrical.

12. The dispenser according to claim 2, wherein the bell-shaped body is fabricated from plastic.

13. A dispenser for liquids comprising:
a valve provided with only one linear channel formed along one longitudinal axis and ending in a first hole which is configured, in use, to break up liquid fed to said one linear channel into small particles and form a jet stream having a predetermined shape, wherein the at least;
a bell-shaped body having an outer surface with a rounded top and extending along a central axis and provided with an axial opening at the rounded top; said bell-shaped body comprising an inner surface from which an elongated member extends substantially concentric with said central axis, the elongated member defining an axial housing configured for receiving the valve; and
wherein said bell-shaped body comprises a discharge chamber arranged between said valve and said axial opening and hydraulically connected with said one linear channel that modifies a shape and direction of said jet stream, wherein the one linear channel is coaxial with a center axis of the discharge chamber;
wherein said valve is disposed entirely within the bell-shaped body that surrounds the valve and the elongated member surrounds the valve.

14. The dispenser according to claim 13, wherein the one linear channel comprises a through hole formed in a body of the valve and wherein the first hole is also formed in the body of the valve and has a width that is different than a width of the one linear channel.

15. The dispenser according to claim 13, wherein the axial housing has a top shoulder against which a top end of the valve seats, the discharge chamber being located between the shoulder and the axial opening.

16. A dispenser for liquids comprising:
a removable valve that comprises a valve body that has only one longitudinal channel formed therein in a form of a linear through hole that ends in a first hole which is configured, in use, to break up liquid fed to said linear through hole channel into small particles and form a jet stream having a predetermined shape;
a bell-shaped body having an outer surface with a rounded top and extending along a central axis and provided with an axial opening at the rounded top; said bell-shaped body comprising an inner surface from which an elongated member extends substantially concentric with said central axis, the elongated member defining an axial housing configured for receiving the, the linear through hole and the first hole being integrally formed in the valve body of the valve and wherein the first hole has a width that is less than a width of the linear through hole, wherein the linear through hole and the first hole are located internally within the bell-shaped body; and
wherein said bell-shaped body comprises a discharge chamber arranged between said valve and said axial opening and hydraulically connected with said linear through hole that modifies a shape and direction of said jet stream through variations in a longitudinal profile of the discharge chamber;
wherein the elongated member surrounds the valve body and has a length greater than a length of the valve body such that the elongated member is located below a bottom edge of the valve body;
wherein the first hole is also formed in and at one end of the body of the valve and has a width that is different than a width of the linear through hole.

17. The dispenser according to claim 16, wherein the valve is disposed entirely within the bell-shaped body.

* * * * *